(12) United States Patent
Patterson et al.

(10) Patent No.: US 6,187,347 B1
(45) Date of Patent: Feb. 13, 2001

(54) COMPOSITION FOR ARRESTING THE FLOW OF BLOOD AND METHOD

(75) Inventors: James A. Patterson; James W. Reding, both of Sarasota, FL (US); John A. Thompson, Nassau (BS); James V. Benson, Reno, NV (US)

(73) Assignee: EcoSafe, LLC., Sarasota, FL (US)

( * ) Notice: Under 35 U.S.C. 154(b), the term of this patent shall be extended for 0 days.

(21) Appl. No.: 09/500,902

(22) Filed: Feb. 9, 2000

(51) Int. Cl.$^7$ ............................ A61K 33/26; A01N 59/16
(52) U.S. Cl. ........................ 424/646; 424/647; 424/648; 424/486; 424/489; 424/484; 424/497
(58) Field of Search ........................ 424/646, 647, 424/648, 484, 486, 489, 497

(56) References Cited

U.S. PATENT DOCUMENTS

| | | |
|---|---|---|
| 2,163,588 | 6/1939 | Cornish . |
| 2,366,007 | * 12/1944 | D'Alelio ............................ 521/33 |
| 2,688,586 | 9/1954 | Eberl . |
| 2,772,999 | 12/1956 | Masci et al. . |
| 2,773,000 | 12/1956 | Masci et al. . |
| 3,206,361 | 9/1965 | Shelley . |
| 3,328,259 | 6/1967 | Anderson . |
| 3,463,320 | * 8/1969 | Patterson ............................ 210/232 |
| 4,265,233 | 5/1981 | Sugitachi et al. . |
| 4,291,980 | * 9/1981 | Patterson ............................ 73/61.41 |
| 4,363,319 | 12/1982 | Altshuler . |
| 4,545,974 | 10/1985 | Thompson . |
| 4,600,574 | 7/1986 | Linder et al. . |
| 4,606,910 | 8/1986 | Sawyer . |
| 4,616,644 | * 10/1986 | Saferstein et al. ............................ 602/48 |
| 4,655,211 | 4/1987 | Sakamoto et al. . |
| 5,474,782 | 12/1995 | Winter et al. . |
| 5,484,913 | 1/1996 | Stilwell et al. . |
| 5,525,498 | 6/1996 | Boctor et al. . |
| 5,643,596 | 7/1997 | Pruss et al. . |
| 5,645,849 | 7/1997 | Pruss et al. . |
| 5,679,372 | 10/1997 | Shimuzu et al. . |
| 5,692,302 | 12/1997 | Martin et al. . |
| 5,763,411 | 6/1998 | Edwardson et al. . |
| 5,800,372 | 9/1998 | Bell et al. . |
| 5,804,428 | 9/1998 | Edwardson et al. . |
| 5,874,479 | * 2/1999 | Martin ............................ 514/724 |
| 5,962,026 | 10/1999 | Edwardson et al. . |
| 5,981,606 | 11/1999 | Martin et al. . |

* cited by examiner

*Primary Examiner*—James O. Wilson
*Assistant Examiner*—Pernell V. Williams
(74) *Attorney, Agent, or Firm*—Charles J. Prescott

(57) ABSTRACT

A composition and method of arresting the flow of blood and other protein containing body fluids flowing from an open wound and for promoting wound healing. In the method, a substantially anhydrous compound of a salt ferrate is provided for a unique use which will hydrate in the presence of blood and body fluid to produce $Fe^{+++}$ thereby promoting clotting when applied to the wound for a time sufficient to arrest substantial further blood and other body fluid flow from the wound. The compound is formed of a salt taken from the group consisting of H, Li, Na, K, Rb, Cs and Fr. However, to decrease or eliminate stinging sensation, the compound may be formed having a salt taken from the group consisting of Be, Mg, Ca, Sr, Ba, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi, Al, As, $NH_4$ and $N(C_4H_9)_4$. The preferred composition also includes a cation exchange material such as sulfonated ion exchange resin as an admixture which will hydrate in the presence of blood and other body fluids to produce $Fe^{+++}$ thereby promoting clotting of the blood and body fluid and to produce oxygen. The cation exchange material produces a scab or protective coating over the wound for protection and enhanced healing. Oxygen produced during the reaction substantially reduces the level of bacteria, virus and fungus at the wound.

28 Claims, No Drawings

COMPOSITION FOR ARRESTING THE FLOW OF BLOOD AND METHOD

BACKGROUND OF THE INVENTION

1. Scope of Invention

This invention relates generally to topically applied agents for promoting blood clotting to arrest blood flow from an open wound, and more particularly to a method and an anhydrous composition which may be applied directly over an open bleeding wound or a wound from which body fluid is flowing, e.g. an open blister, to accelerate flowing blood and body fluid clotting and enhance healing.

2. Prior Art

In addition to conventional bandages, adhesive means, compresses and the like which are applied with pressure directly against a bleeding open wound, considerable effort has been directed toward the development of chemical agents in various forms which accelerate or enhance the coagulation of blood flowing from an open wound to arrest blood flow. Many of these agents are in the "clotting chain", i.e., fibrinogen, thrombin, Factor Vil and the like. Others are based upon the use of collagens. Edwardson, in U.S. Pat. Nos. 5,763,411, 5,804,428, and 5,962,026, for example, teaches the use of fibrin in conjunction with a solid support in the '411 patent, and as an enzyme free sealant in the '428 patent, and as a solid composition substantially free of catalytic enzymes.

Three U.S. Patents invented by Martin, U.S. Pat. Nos. 5,692,302, 5,874,479 and 5,981,606, are generally directed to the use of pyruvate in combination with fatty acids and an oxidant as a therapeutic wound healing composition.

Stilwell, in U.S. Pat. No. 5,484,913 teaches the use of calcium-modified oxidized cellulose to promote faster hemostasis. In U.S. Pat. No. 5,474,782, Winter, et al. teaches a wound healing composition or its salt present in a pharmaceutically acceptable carrier, the preferred embodiment being a salt of sodium. Winter provides a wound dressing with a taspine compound for promoting healing rather than clotting.

In U.S. Pat. No. 2,163,588, Cornish teaches a wound pad having very fine fibers carrying a viscous agent and a septic for arresting and clotting blood flow. Eberl, et al., in U.S. Pat. No. 2,688,586, teaches an improved hemostatic surgical dressing with alginic acid as a clotting agent. Masci, et al. in U.S. Pat. Nos. 2,772,999 and 2,773,000 also teaches hemostatic surgical dressing including a pad and free acid cellulose glycolic acid.

A patent for another hemostatic wound dressing is taught by Shelley in U.S. Pat. No. 3,206,361 having an active agent in the form of methylaminoacetocatechol hydrochloride. Likewise, Anderson, in U.S. Pat. No. 3,328,259, another wound dressing containing a film of cellulose glycolic acid ether is provided as the hemostatic agent.

The hemostatic agent taught by Sugitachi, et al. as disclosed in U.S. Pat. No. 4,265,233 is blood coagulation Factor VIII plus either fibrin or thrombin. A ready-to-use bandage is taught by Altshuler in U.S. Pat. No. 4,363,319 which also contains thrombin as an active agent, the bandage all of which is contained within a sealed package.

Invented by Lindner, et al., a wound pad which is impregnated with tissue-compatible protein such as collagen and lyophilized Factor XIII, thrombin and fibrinogen, are taught in U.S. Pat. No. 4,600,574. The use of collagen as a hemostatic agent within a pad that has been freeze dried is taught by Sawyer in U.S. Pat. No. 4,606,910.

In U.S. Pat. No. 4,616,644, Saferstein, et al. teaches the use of an adhesive bandage with high molecular weight polyethylene oxide applied to the surface of the perforated plastic film wound release cover of the bandage to arrest blood flow from minor cuts. Yet another hemostatic agent including a carrier in the shape of a flake or fiber having thrombin and Factor XIII affixed thereto is taught by Sakamoto in U.S. Pat. No. 4,655,211. The use of an ultra-pure, clean thrombin solution as a hemostatic agent is taught in U.S. Pat. No. 5,525,498 invented by Boctor. Two recent patents invented by Pruss, et al., U.S. Pat. Nos. 5,643,596 and 5,645,849 both teach the use of hemostatic dressings which incorporate thrombin and epsilon aminocaproic acid (EACA) and calcium chloride on gelatin.

An absorbable spun cotton-like topical hemostat is taught by Shimuzu, et al. in U.S. Pat. No. 5,679,372. This disclosure is directed to an absorbable dressing made of acetocollagen fibers which are innately adhesive to a bleeding surface. In a patent to Bell, et al, U.S. Pat. No. 5,800,372, a dressing made of microfibrillar collagen and a superabsorbant polymer provides both blood absorption and clotting inducement.

One embodiment of the present invention utilizes an improved ion exchange resin, preferably in the form of a styrene divinylbenzene copolymer which has been sulfonated. The collective teaching of making this prior art resin is to be found in an earlier patent to co-inventor, Patterson, U.S. Pat. No. 4,291,980. This method disclosed was based at least in part on the production of spherical beads comprised of copolymer styrene and divinylbenzene as taught in U.S. Pat. Nos. 2,366,007 and 3,463,320. This collective teaching is incorporated herein by reference. An improvement better adapting this resin to the present invention is in the form of substantially reduced cross-linking down to about 0.25%.

Another primary aspect of the present invention incorporates a salt ferrate, preferably potassium ferrate ($2K_2FeO_4$). The teaching of a process for producing alkaline metal ferrates is taught by another co-inventor, Thompson, in U.S. Pat. No. 4,545,974. This teaching is also incorporated herein by reference.

It is submitted that the above-referenced prior art, either taken individually or collectively in any combination thereof fail to teach a flowing blood or body fluid clotting agent which includes an admixture of a salt ferrate which produces a trivalent $Fe^{+++}$ ion which reacts with the blood to accelerate coagulation and clott ing of the blood. Moreover, the utilization of an insoluble cation exchange material, e.g. a sulfonated ion exchange resin, in combination with the salt ferrate, additionally produces a protective covering over the wound and also produces oxygen which acts as an antibacterial, antiviral and antifungal agent. Further, the presence of selected salts neutralize hydroxide radicals as clotting occurs so as to eliminate any substantial stinging sensation.

BRIEF SUMMARY OF THE INVENTION

This invention is directed to a composition and method of arresting the flow of blood and other body fluid from an open wound and for promoting wound healing. In the method, a substantially anhydrous compound of a salt ferrate is provided for unique use which will hydrate in the presence of blood and other body fluid with protein to produce $Fe^{+++}$ thereby promoting clotting of the blood and other body fluids when applied to the op en wound for a time sufficient to effect clotting of the blood or body fluid to arrest substantial further flow from the wound. The compound is formed of a monovalent, divalent, or trivalent salt ferrate ($M_2 Fe O_4$, $M_2' Fe O_4$ or $M_2' Fe O_4$) taken from the cationic group consisting of H, Li, Na, K, Rb, Cs and Fr. However, to decrease or eliminate stinging sensation, the compound may be formed having a salt taken from the cationic group consisting of Be, Mg, Ca, Sr, Ba, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi, Al, As, $NH_4$, and $N(C_4H_9)_4$. The preferred composition includes the substantially anhydrous salt ferrate compound and a sulfonated ion exchange resin as an admixture which will hydrate in the presence of blood to produce $Fe^{+++}$, thereby promoting clotting of the blood and oxygen. The resin produces a scab or protective coating over the wound for protection and enhanced healing. Oxygen produced during the reaction substantially reduces the level of bacteria, virus and fungus at the wound.

It is therefore an object of this invention to provide a method of utilizing a salt ferrate as a blood clotting agent for arresting blood flow from an open surface wound.

It is another object of this invention to provide a method of arresting blood and body fluid flow utilizing a salt ferrate composition which is substantially sting-free when applied onto an open wound.

It is still another object of this invention to provide a composition utilizing a salt ferrate combined with an insoluble cation exchange material to arrest blood flow from an open skin wound.

Another object of this invention is to provide a composition of a salt ferrate and an insoluble cation exchange material which in addition to promoting blood clotting to arrest blood flow from an open wound, also provides antiseptic and a clumping or scabbing over the wound as a protective coating for the injury.

It is yet another object of this invention to provide a composition for promoting clotting of blood flowing from an open skin wound which minimizes or eliminates any sting associated with its application.

Still another object of this invention is to provide a localized rapid forming protective coating or covering that has antibacterial, antifungal and antiviral properties.

In accordance with these and other objects which will become apparent hereinafter, the instant invention will now be described.

DETAILED DESCRIPTION OF THE INVENTION

Mechanism of Blood Coagulation

The following is offered as a brief explanation of one possible mechanism which would explain the effectiveness of the present invention as described herebelow in full detail.

The plasma of circulating blood normally remains a liquid with it's colloidal protein in the solid state. After albumin, the second most abundant protein in mammalian blood is a long, large molecule called fibrinogen. A series of enzymatic reactions take place during the clotting of blood. An inactive plasma enzyme (prothrombin) is converted into an active enzyme (thrombin) which, in turn, removes two pairs of amino acid groups from each fibrinogen molecule, converting into a molecule called fibrin monomer. Fibrin monomer then links together to form a polymer, which is the visible clot. The reactions can be summarized as follows:

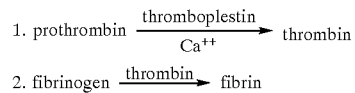

It is known that the decomposition of potassium ferrate produces the finest particles of iron oxide ($Fe_2O_3$) available. (See U.S. Pat. No. 4,545,974). Upon addition to water, $K_2FeO_4$ becomes $Fe^{+++}$ in the form of FeOOH, which upon drying, yields $Fe_2 O_3$. The FeOOH (or $Fe_2 O_3 H_2O$) is a solid in suspension and this ultra-fine material seems to be an ideal irritant for platelet membranes, thereby releasing the prothroplastin that is needed to initialize clotting. It is possible that they may tend to rupture the platelets themselves, thereby causing a massive release of clotting factors as does the rough surface of a wound achieve the same end.

It is possible that the $Fe^{+++}$ion itself may aid in coagulation of blood. Trivalent ions, by lowering the zeta potential of a particle in solution, allow the particles (platelets) to clump more easily. Platelets are small disks of cytoplasm found in the blood of mammals. After a wound is received they begin to clump and stick around the wound area, causing the clumping and sticking of another cytoplasmic component, the thrombocycte. During this clumping process, certain phospholipids from the membrane of the platelets contribute to the overall clotting process, combined with the inactive plasma enzyme, Factor XII. Mechanical abrasion of the platelets is important in freeing the phospholipid component from the platelets.

Range of Useful Salt Ferrates

Initially, applicants have found that the utilization of potassium ferrate, again likely based upon the above-recited theory, effectively accomplishes the accelerated clotting of blood flowing from an open wound. The apparent chemical ferrate reaction with water found in blood is as follows:

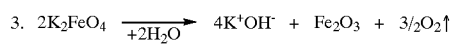

One of the important results is the production of the trivalent $Fe^{+++}$ ion which appears to be the beneficial clotting agent provided in this aspect of this invention. Moreover, it has been determined that the present invention acts on all body fluids containing protein, such as that which flows from an open skin blister or burn.

A broadening of this aspect of the inventive compound would be to substitute the potassium salt with others which possess the same cation properties as does the potassium cation. Those salt elements which will substitute for the potassium cation are shown in Tables I and II herebelow.

TABLE I

| | |
|---|---|
| H | Hydrogen |
| Li | Lithium |
| Na | Sodium |
| K | Potassium |
| Rb | Rubidium |
| Cs | Cesium |
| Fr | Francium |

TABLE II

| | | | | | |
|---|---|---|---|---|---|
| Be | Beryllium | Mg | Magnesium | Ca | Calcium |
| Sr | Strontium | Ba | Barium | Ra | Radium |
| Ti | Titanium | V | Vanadium | Cr | Chromium |
| Mn | Manganese | Fe | Iron | Co | Cobalt |
| Ni | Nickel | Cu | Copper | Zn | Zinc |
| Ga | Gallium | Ge | Geranium | Zr | Zirconium |
| Nb | Niobium | Mo | Molybdenum | Tc | Technetium |
| Ru | Ruthenium | Rh | Rhodium | Pd | Palladium |
| Ag | Silver | Cd | Cadmium | In | Indium |
| Sn | Tin | Hf | Hafnium | Ta | Tantalum |
| W | Tungsten | Re | Rhenium | Os | Osmium |
| Ir | Iridium | Pt | Platinum | Au | Gold |
| Hg | Mercury | Tl | Thallium | Pb | Lead |
| Bi | Bismuth | Al | Aluminum | As | Arsenic |
| $NH_4$ | Cation | $N(C_4H_9)_4$ | Cation | | |

In addition to the above salts in the cation form, all zeolites, sulfonated coal, and natural reoccurring membranes such as protein membranes will also act in compound form with ferrate to release the trivalent $Fe^{+++}$ ion to effect blood and body fluid coagulation.

Eliminating Stinging Effect

In utilizing the $K_2 Fe O_4$ as above described to arrest blood flow from a bleeding wound, equation 3 shows the presence of hydroxide $(OH)^{31}$ radicals which are produced. The hydroxide $(OH)^-$ radicals remain present in equation 5 and cause stinging at the wound site. Moreover, all of the cation salts of Table I produce the same result, i.e. stinging caused by the presence of the hydroxide ion.

All of the cation salts listed in Table II, however, produce a slightly altered chemical reaction which neutralizes all of the hydroxide ions produced. For example, using a calcium cation salt to replace the potassium cation causes the following chemical reaction with water in blood:

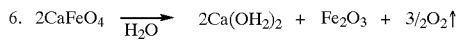

6. $2CaFeO_4 \xrightarrow{H_2O} 2Ca(OH_2)_2 + Fe_2O_3 + 3/2 O_2 \uparrow$

As can be observed from Equation 6, no hydroxide ions are produced. Rather, all are neutralized and combined with calcium as shown in the equation.

As provided by the above compounds, a method of arresting blood and body fluid flow from an open skin wound is provided. An effective amount of any of the above salt ferrates, and preferably potassium ferrate in powder form, is applied directly onto the wound to interact with flowing blood or body fluid to accelerate its clotting.

Salt Ferrate Combined With Resin

Although the above methodology and utilization of a salt ferrate greatly enhances blood clotting, the wound nonetheless remains opened and generally unprotected unless the salt ferrate is combined with a carrier such as a BAND-AID, bandage, cotton member and the like which has been impregnated or coated with a dry powder taken from of one of the above chosen salt ferrate compositions.

By the addition of an ion exchange resin R with the salt ferrate, an additional benefit of scabbing or depositing of a substance produced by the reaction with water in the blood is accomplished over the open wound. Details of the composition and method of producing the preferred ion exchange resin R in the form of styrene divinylbenzene are disclosed in the previously referenced patents and are herein incorporated by reference. As described in formulas herebelow, the resin R may be shown in its chemical form or generally designated by the symbol "R" for simplicity. The ion exchange resin R is sulfonated as is shown in chemical terms in each chemical equation herebelow.

An acid form of the sulfonated ion exchange resin R in acid form is shown symbolically as follows:

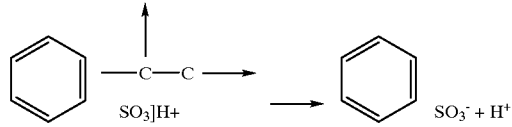

When the preferred hydrogen form of this sulfonated ion exchange resin R is in the presence of the salt ferrate and water within blood, the following reaction serves to neutralize the hydroxyl ions produced in equation 3 above.

7.

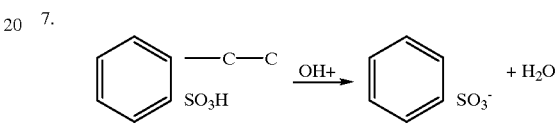

In addition to neutralizing hydroxyl ions by the presence of even trace amounts of the resin R to decrease or totally eliminate the stinging effect, excess trivalent $Fe^{+++}$ ions interact with the resin as follows:

8.

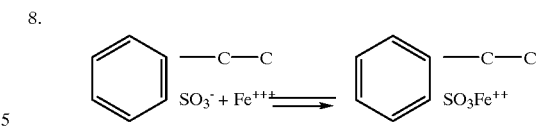

Thus, excess trivalent Few charged ion cross links with the clotting blood in accordance with the following equation:

9.

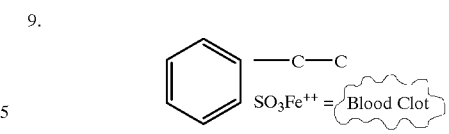

The amino acid in the blood protein are shown to interact with the resin:

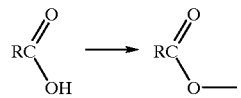

The $K_2 Fe O_4$ should be hygroscopic, small particles approximately 50 to 100 mesh size for best surface area. The ion exchange resin R is preferably in an acid form with some substitute Ca calcium ions as shown in equations 6 to 9. The cross linking of the resin R should be below 4.0 and as low as 0.25% and hygroscopic. The weight ratio should favor the dry ion exchange resin R by at least 4 to 1 of dry salt ferrate. The ion exchange resin R is preferably a cation exchange resin.

In another embodiment, a small amount of divalent calcium Ca++ may be added as an additional anticoagulant.

Heparin-EDTA (Ethylene Dismine Tetracacitic Acid) potassium oxalate are anticoagulants and are ionic in action on the divalent Calcium $Ca^{++}$ and trivalent ion $Fe^{+++}$ to prevent clotting. By supplying excess of these ions, i.e. $Fe^{+++}$, clotting can be induced. Also, in addition to the hydrogen form of the resin R3-

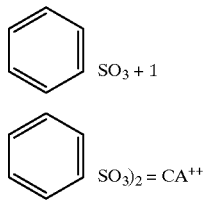

a given ratio of the calcium salt can supply excess of this ion to further induce blood clotting. The ferrate in contact with the blood-) water on the skin forms $O_2$ which is a strong disinfectant to the cut.

Summary of Benefits

By combining even a trace amount of the above-described sulfonated resin $RSO_3$ as an admixture with potassium ferrate ($K_2FeO_4$), the following benefits are derived:
1. The trivalent $Fe^{+++}$+3 $RSO_3$ produces blood clotting and blood flow stoppage;
2. Oxygen produced by the reaction serves as an antibacterial, antiviral and antifungal agent;
3. The blood clotting with resin R produces a scab that acts as a protective coating for the wound;
4. Even trace amounts of resin R in this admixture neutralizes hydroxyl ions to prevent stinging.

EXPERIMENTAL RESULTS

A ferrate—ion exchange resin admixture (moisture free) was prepared for direct application to a bleeding injury as follows:

| | |
|---|---|
| 200μ ion exchange resin in acid form (dry) | 0.79 g |
| 50 ms $K_2FeO_4$ (dry) | 0.23 g |
| Total | 1.02 g |

The cation exchange resin R was prepared in the washed hydrogen form, and then dried at 110° for 24 hours and powdered in grinder to about 100 mesh.

This composition was then applied directly to a fresh bleeding finger wound produced by a skin lancet having a penetration of 1.6–2.2 mm. The subject was 77 years old, skin condition non-flexible. Wound blood flow was at a rate of 0.206g/30 seconds or 0.0412g per minute to 0.0606g per minute.

When a single penetration of the skin was made and blood flow started at 0.0412 to 0.0605 g per minute, application of 5 sec. of the above resin-ferrate composition directly to the wound dropped blood to zero as determined with a blot pickup of 0.0020g within 1.0 minute. The resin-ferrate applied was on the order of 0.0175–0.0170 grams, forming a hard protecting sterilized coating over the penetration injury by the time that blood flow from the wound was stopped.

Dosage Economy

Pretreatment Blood Flow . . . 0.0305 g blood/30 sec. (0.0605 g/min) After treatment Blood Flow . . . 0.0010 g blood/30 sec. (0.0028 g/min Dosage . . . 0.0174 g of anhydrous ferrate and resin admixture was used to treat wound.

At this dosage, a 30 g quantity of the composition will provide approximately 1724 separate treatments.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:
1. A method of arresting the flow of blood from a bleeding wound comprising the steps of:
   A. providing a substantially anhydrous compound of a salt ferrate which will hydrate in the presence of blood to produce $Fe^{+++}$ thereby promoting clotting of the blood;
   B. applying said compound to the wound for a time sufficient to effect sufficient clotting of the blood to arrest substantial further blood flow from the wound.
2. The method of claim 1, wherein:
   said compound provided in Step A is formed of a salt taken from the group consisting of H, Li, Na, K, Rb, Cs and Fr.
3. The method of claim 1, wherein:
   said compound provided in Step A is formed having a salt taken from the group consisting of Be, Mg, Ca, Sr, Ba, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi, Al, As, $NH_4$ and $N(C_4H_9)_4$.
4. The method of claim 1, wherein:
   said compound provided in Step A is formed of a salt taken from the group consisting of H, Li, Be, Na, Mg, K, Ca, Rb, Sr, Cs, Ba, Fr, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi, Al, As, $NH_4$ and $N(C_4H_9)_4$.
5. The method of claim 1, wherein:
   said compound provided in Step A is $K_2$ Fe $O_4$.
6. The method of claim 1, wherein:
   said compound provided in Step A is formed of a salt which combines with water in the blood to eliminate substantially all hydroxide ($OH^-$) which cause a stinging sensation.
7. A method of promoting healing of a bleeding wound comprising the steps of.
   A. providing a substantially anhydrous compound of a salt ferrate and an insoluble cation exchange material which will hydrate in the presence of blood to produce $Fe^{+++}$, thereby promoting clotting of the blood, and oxygen;
   B. promoting blood clotting, followed by blood flow stoppage, by applying said compound to the bleeding wound;
   C. substantially reducing the level of bacteria, virus and fungus at the wound during Step B by the presence of said oxygen;
   D. forming a protective coating over the wound during Step B.
8. The method of claim 7, wherein:
   said compound provided in Step A is formed of a salt taken from the group consisting of H, Li, Na, K, Rb, Cs and Fr.

9. The method of claim 7, wherein:

said compound provided in Step A is formed having a salt taken from the group consisting of Be, Mg, Ca, Sr, Ba, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi Al, As, $NH_4$ and $N(C_4H_9)_4$.

10. The method of claim 7, wherein:

said compound provided in Step A is formed of a salt taken from the group consisting of H, Li, Be, Na, Mg, K, Ca, Rb, Sr, Cs, Ba, Fr, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi Al, As, $NH_4$ and $N(C_4H_9)_4$.

11. The method of claim 7, wherein:

said compound provided in Step A is $K_2 Fe O_4$.

12. The method of claim 7, wherein:

said compound provided in Step A includes a salt which combines with water in the blood to eliminate substantially all hydroxide ($OH^-$) which cause a stinging sensation.

13. The method of claim 7, wherein:

said insoluble exchange material is a cation exchange resin.

14. A composition useful in promoting healing of a bleeding wound consisting essentially of:

a substantially anhydrous salt ferrate compound combined with an effective amount of an insoluble cation exchange material.

15. A composition as set forth in claim 14, wherein:

said cation exchange material is a resin which is cross linked in the range of 0.25% to 4%.

16. A composition as set forth in claim 15, wherein:

said ion exchange resin is styrene divinylbenzene.

17. A composition as set forth in claim 14, wherein:

said cation exchange material is present in a trace amount.

18. A composition as set forth in claim 14, wherein:

said cation exchange material is hygroscopic and of a particle size from about 50 mesh to about 100 mesh.

19. A composition as set forth in claim 14, wherein:

said salt ferrate is potassium ferrate and said cation exchange material is styrene divinylbenzene.

20. A hemostatic agent adapted to be applied directly onto a bleeding wound comprising:

an effective amount of a salt ferrate combined with an effective amount of an insoluble cation exchange material, said salt ferrate combining with blood to form a trivalent $Fe^{+++}$ ion which promotes blood clotting at the wound, said cation exchange material forming a protective cover over the wound as said trivalent $Fe^{+++}$ ion is formed.

21. A hemostatic agent as set forth in claim 20, further comprising:

a carrier or support comprising a bandage which has applied to its surface an effective quantity of said hemostatic agent in an anhydrous form.

22. A hemostatic agent as set forth in claim 20, wherein:

said cation exchange material is an ion exchange resin which is cross linked from about 0.25% to about 4%.

23. A hemostatic agent as set forth in claim 22, wherein:

said ion exchange resin is styrene divinylbenzene.

24. A hemostatic agent as set forth in claim 20, wherein:

said cation exchange material is present in a trace amount.

25. A hemostatic agent as set forth in claim 20, wherein:

said cation exchange material is hygroscopic and of a particle size from about 50 mesh to about 100 mesh.

26. A hemostatic agent as set forth in claim 20, wherein:

said salt ferrate is potassium ferrate and said cation exchange material is styrene divinylbenzene.

27. The method of claim 1, wherein:

said anhydrous compound is a monovalent, divalent or a trivalent salt ferrate.

28. The method of claim 7, wherein:

said anhydrous compound is a monovalent, divalent or a trivalent salt ferrate.

* * * * *